United States Patent [19]

Sugo et al.

[11] Patent Number: 5,852,153
[45] Date of Patent: Dec. 22, 1998

[54] TRIMETHYLSILOXY GROUP-CONTAINING POLYSILOXANE AND A PROCESS FOR PRODUCING THE SAME

[75] Inventors: Michihiro Sugo, Annaka; Hisashi Aoki, Takasaki, both of Japan

[73] Assignee: Shin-Etsu Chemical Co., Ltd., Tokyo, Japan

[21] Appl. No.: 923,082

[22] Filed: Sep. 4, 1997

Related U.S. Application Data

[62] Division of Ser. No. 678,755, Jul. 11, 1996, Pat. No. 5,693,735.

[30] Foreign Application Priority Data

Jul. 12, 1995 [JP] Japan ................................. 7-199012
Jul. 14, 1995 [JP] Japan ................................. 7-201505

[51] Int. Cl.⁶ ................................................. C08G 77/08
[52] U.S. Cl. ............................... 528/14; 528/18; 528/34; 528/37; 556/460
[58] Field of Search ........................... 528/14, 18, 34, 528/37; 556/460

[56] References Cited

U.S. PATENT DOCUMENTS 5,449,800  9/1995  Shimada et al. .
5,475,076  12/1995  Braun et al. .............................. 528/14
5,496,961  3/1996  Dauth et al. .

*Primary Examiner*—Melvyn I. Marquis
*Attorney, Agent, or Firm*—Oblon, Spivak, McClelland, Maier & Neustadt, P.C.

[57] ABSTRACT

A novel cyclotrisiloxane having the following general formula (1) and a novel copolymer synthesized using the cyclotrisiloxane are provided. The copolymer is excellent in low-temperature characteristics, heat resistance, temperature-viscosity characteristics, and compatibility with various fluids and is particularly useful as a starting material for use in cosmetics and greases.

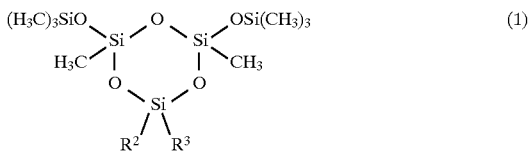

wherein $R^2$ is a hydrogen atom, an alkyl group, an aryl group, an aralkyl group, a halogenated alkyl group, an alkenyl group, an acryloyloxypropyl group or a methacryloyloxypropyl group, and $R^3$ is a methyl group or a phenyl group.

3 Claims, 10 Drawing Sheets

TRIMETHYLSILOXY GROUP-CONTAINING POLYSILOXANE AND A PROCESS FOR PRODUCING THE SAME

This is a Division of application Ser. No. 08/678,755 filed on Jul. 11, 1996 U.S. Pat. No. 5,693,735.

BACKGROUND OF THE INVENTION

1. Field of the Invention

The present invention relates to a novel cyclotrisiloxane containing a trimethylsiloxy group and a novel organosiloxane copolymer containing a trimethylsiloxy group which is synthesized using said cyclotrisiloxane as a starting material, and to a process for producing each of the cyclotrisiloxane and the organosiloxane copolymer.

2. Description of the Prior Art

Conventionally known cyclotrisiloxanes include, for example, those represented by the following general formula:

wherein $R^1$ is independently an unsubstituted or substituted alkyl group having 1 to 3 carbon atoms, and X is a cyclohexyl group or an alkyl group represented by the following general formula:

wherein m is an integer of 4 to 15 [see Japanese Pre-examination Patent Publication (Kokai) No. 6-279466]. However, there has not been known a cyclotrisiloxane containing a trimethylsiloxy group bonded to silicon atoms constituting a ring thereof.

While, polysiloxanes are produced by equilibrium reaction of the conventional cyclic polysiloxane as mentioned above or by cohydrolysis condensation reaction of chlorosilane. However, in these methods, cleavage and polymerization reactions proceed at random. Consequently, these methods can not control the structure of the resulting polysiloxane and also can not produce an organosiloxane copolymer containing a desired amount of a trimethylsiloxy group. Thus, a branched polysiloxane containing a trimethylsiloxy group at the side chain thereof has not yet been known.

SUMMARY OF THE INVENTION

An object of the present invention is to provide a novel trimethylsiloxy group-containing polysiloxane which is a novel cyclotrisiloxane containing a trimethylsiloxy group bonded to silicon atoms constituting a ring thereof, and a process for producing the same.

Another object of the present invention is to provide a novel trimethylsiloxy group-containing polysiloxane which is a novel organosiloxane copolymer containing a trimethylsiloxy group bonded to silicon atoms at a side chain thereof, and a process for producing the same.

A first aspect of the present invention is a cyclotrisiloxane represented by the following general formula (1):

wherein $R^2$ is a hydrogen atom, an alkyl group, an aryl group, an aralkyl group, a halogenated alkyl group, an alkenyl group, an acryloyloxypropyl group or a methacryloyloxypropyl group, and $R^3$ is a methyl group or a phenyl group.

A second aspect of the present invention is a process for producing the cyclotrisiloxane of said general formula (1), comprising reacting a silanol group-containing organosiloxane represented by the following formula (2):

with a dichlorosilane represented by the following general formula (3):

wherein $R^2$ and $R^3$ are as define above, in the presence of a HCl-capturing agent (i.e., HCl-scavenger).

A third aspect of the present invention is an organosiloxane copolymer represented by the following general formula (4):

wherein $R^4$ is a monovalent hydrocarbon group; $R^5$ and $R^6$ are independently a monovalent hydrocarbon group or a substituted alkyl group in which at least part of hydrogen atoms has been substituted with a halogen atom (namely, a halogenated alkyl group); A is a hydrogen atom or an organosilyl group represented by the following general formula:

wherein plural $R^7$ are independently a hydrogen atom or a monovalent organic group, provided that at least one of plural $R^7$ is a monovalent organic group; a is an integer of 4 or more; b is an integer of 2 or more; and c is an integer of 0 or more.

A fourth aspect of the present invention is a process for producing the organosiloxane copolymer of said general formula (4), comprising the steps of subjecting a cyclotrisiloxane where in the general formula (1), $R^1$ and $R^2$ are each a methyl group, namely, a cyclotrisiloxane represented by the following formula (5):

optionally together with a cyclotrisiloxane represented by the following general formula (6):

(6)

wherein $R^5$ and $R^6$ are independently a monovalent hydrocarbon group or a halogenated alkyl group, to ringopening polymerization in the presence of a lithium compound represented by the following general formula (7):

$$R^4(R^8R^9SiO)_n Li \quad (7)$$

wherein $R^4$ is a monovalent hydrocarbon group, $R^8$ and $R^9$ are independently a monovalent hydrocarbon group or a halogenated alkyl group, and n is an integer of 0 or more, and adding to the resulting reaction mixture an acid or an organohalosilane represented by the following general formula (8):

$$XSi(R^7)_3 \quad (8)$$

wherein X is a halogen atom, and plural $R^7$ are independently a hydrogen atom or a monovalent organic group, provided that at least one of plural $R^7$ is a monovalent organic group, to stop the ringopening polymerization.

The cyclotrisiloxanes of the present invention are novel compounds and are useful as a starting material for synthesizing silicone fluids excellent in low-temperature characteristics.

In a preferred embodiment, upon synthesizing a silicone fluid using, for example, the cyclotrisiloxane represented by the formula (5), the novel organosiloxane copolymer represented by the general formula (4) can be obtained. The copolymer is excellent in low-temperature characteristics, heat resistance, temperature-viscosity characteristics, and compatibility with various fluids and is particularly useful as a starting material for use in cosmetics and greases.

BRIEF DESCRIPTION OF THE DRAWINGS

FIG. 10 is a DSC chart of copolymers and the like.

DESCRIPTION OF THE PREFERRED EMBODIMENTS

The present invention will now be described in detail.

Cyclotrisiloxane

The cyclotrisiloxane of the present invention is represented by said general formula (1). In this formula, $R^2$ is a hydrogen atom, an alkyl group, an aryl group, an aralkyl group, a halogenated alkyl group, an alkenyl group, an acryloyloxypropyl group or a methacryloyloxypropyl group, and $R^2$ is a methyl group or a phenyl group.

The alkyl group of said $R^2$ includes, for example, an alkyl group having 1 to 12 carbon atoms such as methyl, ethyl, propyl, isopropyl, butyl, isobutyl, tert-butyl, pentyl, neopentyl, hexyl, heptyl, octyl, nonyl, decyl and dodecyl groups, and typically an alkyl group having 1 to 8 carbon atoms such as methyl, ethyl, propyl, isopropyl, butyl, hexyl and octyl groups.

The aryl group of said $R^2$ includes, for example, an aryl group having 6 to 18 carbon atoms such as phenyl, tolyl, xylyl, naphthyl and biphenylyl groups, and typically an aryl group having 6 to 12 carbon atoms such as phenyl, tolyl and naphthyl groups.

The aralkyl group of said $R^2$ includes, for example, an aralkyl group having 7 to 12 carbon atoms such as benzyl, phenylethyl, phenylpropyl and methylbenzyl groups, and typically an aralkyl group having 7 to 9 carbon atoms such as benzyl and phenylpropyl groups.

The halogenated alkyl group of said $R^2$ includes, for example, a halogenated alkyl group having 1 to 12 carbon atoms such as chloromethyl, 2-bromoethyl, 3-chloropropyl, 3,3,3-trifluoropropyl and 3,3,4,4,5,5,6,6,6-nonafluorohexyl groups, and typically a halogenated alkyl group having 1 to 6 carbon atoms such as 3-chloropropyl, 3,3,3-trifluoropropyl and 3,3,4,4,5,5,6,6,6-nonafluorohexyl groups.

The alkenyl group of said $R^2$ includes, for example, an alkenyl group having 2 to 12 carbon atoms such as vinyl, allyl, propenyl, isopropenyl, butenyl, isobutenyl, hexenyl and cyclohexenyl groups, and typically an alkenyl group having 2 to 6 carbon atoms such as vinyl, allyl and hexenyl groups.

Among these $R^2$ groups, particularly preferred are a hydrogen atom, a methyl group, a vinyl group and a phenyl group in view of being capable of obtaining silicone fluids more superior in low-temperature characteristics.

Specific examples of the cyclotrisiloxane of the present invention are not particularly limited but include, for example, those represented by the following formulas:

and wherein Ph stands for a phenyl group.

Process for Producing Cyclotrisiloxanes

The process for producing a cyclotrisiloxane according to the present invention comprises reacting a silanol group-containing organosiloxane represented by said formula (2) and a dichlorosilane represented by said general formula (3) in the presence of a HCl-capturing agent.

The dichlorosilane includes, for example, methyldichlorosilane, dimethyldichlorosilane, methylethyldichlorosilane, methylpropyldichlorosilane, methylhexyldichlorosilane, methyloctyldichlorosilane, methldecyldichlorosilane, methyldodecyldichlorosilane, methylphenyldichlorosilane, diphenyldichlorosilane, methylbenzyldichlorosilane, (2-phenylpropyl) methyldichlorosilane, 3,3,3-trifluoropropyl) methyldichlorosilane, methylvinyldichlorosilane, acryloyloxypropylmethyldichlorosilane, methacryloyloxypropylmethyldichlorosilane, phenyldichlorosilane, ethylphenyldichlorosilane and vinylphenyldichlorosilane.

The amount of the dichlorosilane used is generally 0.8 to 1.2 moles, preferably 0.9 to 1.0 mole per mole of the silanol group-containing organosiloxane.

The HCl-capturing agent is not particularly limited as long as it can form a stable salt together with hydrochloric acid and includes, for example, ammonia and an amine compound such as dimethylamine, triethylamine and pyridine. The amount of the HCl-capturing agent used is 2 to 3 moles, preferably 2 to 2.5 moles, per mole of the dichlorosilane. The reaction of the silanol group-containing organosiloxane with the dichlorosilane proceeds even if a solvent is not used, but the use of a solvent results in obtaining the cyclotrisiloxane of the present invention in a good yield. The solvent is not particularly limited as long as it has compatibility with the silanol group-containing organosiloxane and dichlorosilane and includes, for example, ketones such as acetone and methyl ethyl ketone; ether solvents such as diethyl ether, tetrahydrofuran and 1,4-dioxane; organic solvents such as toluene, xylene and hexane. They may be used singly or in a combination of two or more thereof. The reaction temperature is preferably 0° to 20° C. By setting the temperature in this range, it is possible that the reaction proceeds smoothly. The reaction time may be about 10 minutes to 4 hours after charging the predetermined starting materials into a reaction vessel.

The thus obtained cyclotrisiloxane of the present invention is useful as a starting material for synthesizing silicone fluids capable of using as greases and sealings superior in particularly low-temperature characteristics.

Now, an organosiloxane copolymer obtained when using the cyclotrisiloxane where in the general formula (1) $R^1$ and $R^2$ are each a methyl group, as a starting material will be described hereinafter.

Organosiloxane Copolymer

The copolymer of the present invention is a copolymer represented by said general formula (4) having, as a repeating unit, at least one unit selected from the group consisting of a unit (hereinafter, referred to as $D^1$ unit) represented by the following formula:

a unit (hereinafter, referred to as $D^2$ unit) represented by the following formula:

and a unit (hereinafter, referred to as $D^3$ unit) represented by the following formula:

and further optionally in addition to these units, having, as a repeating unit, a unit (hereinafter, referred to as $D^4$ unit) represented by the following formula:

wherein $R^5$ and $R^6$ are as defined above.

Typical examples of the copolymer include, for example, copolymers represented by the following formulas:

wherein $R^4$, A, $D^1$, $D^2$, $D^3$, $D^4$ and b are as defined above, and d, e and f are each an integer of 1 or more, preferably 2 to 150.

These copolymers may be a random copolymer or a block copolymer.

In the general formula (4), the monovalent hydrocarbon of $R^4$ includes, for example, alkyl, cycloalkyl, aryl, aralkyl, alkenyl, acryloyloxypropyl and methacryloyloxypropyl groups.

The alkyl group of said $R^4$ includes, for example, an alkyl group having 1 to 12 carbon atoms such as methyl, ethyl, propyl, isopropyl, butyl, isobutyl, tert-butyl, pentyl, neopentyl, hexyl, heptyl, octyl, nonyl, decyl and dodecyl groups, and typically an alkyl group having 1 to 8 carbon atoms such as methyl, propyl, hexyl and octyl groups.

The cycloalkyl group of said R4 includes, for example, a cycloalkyl group having 3 to 12 carbon atoms such as cyclopentyl, cyclohexyl and cycloheptyl groups, and typically a cycloalkyl group having 5 to 8 carbon atoms such as cyclopentyl, cyclohexyl and cyclooctyl groups.

The aryl group of said $R^4$ includes, for example, an aryl group having 6 to 18 carbon atoms such as phenyl, tolyl, xylyl, naphthyl and biphenylyl groups, and typically an aryl group having 6 to 12 carbon atoms such as phenyl, tolyl and naphthyl groups.

The aralkyl group of said $R^4$ includes, for example, an aralkyl group having 7 to 12 carbon atoms such as benzyl, phenylethyl, phenylpropyl and methylbenzyl groups, and typically an aralkyl group having 7 to 9 carbon atoms such as benzyl and phenylpropyl groups.

The alkenyl group of said $R^4$ includes, for example, an alkenyl group having 2 to 12 carbon atoms such as vinyl, allyl, propenyl, isopropenyl, butenyl, isobutenyl, hexenyl and cyclohexenyl groups, and typically an alkenyl group having 2 to 6 carbon atoms such as vinyl, allyl and hexenyl groups.

The monovalent hydrocarbon group of $R^5$ or $R^6$ includes the same groups as exemplified in said $R^4$. Particularly preferable monovalent hydrocarbon groups as $R^5$ or $R^6$ include a methyl group, a phenyl group and a vinyl group. The halogen-substituted alkyl group of $R^5$ or $R^6$ includes, for example, a halogen-substituted alkyl group having 1 to 6 carbon atoms such as chloromethyl, 2-bromoethyl, 3-chloropropyl, 3,3,3-trifluoropropyl and 3,3,4,4,5,5,6,6,6-nonafluorohexyl groups.

The organosilyl group of A is represented by the following general formula:

wherein plural $R^7$ are independently a hydrogen atom or a monovalent organic group, provided that at least one of plural $R^7$ is a monovalent organic group.

The monovalent organic group of $R^7$ includes, for example, the same monovalent organic group and halogen-substituted alkyl group as in $R^5$ or R6 and in addition thereto, the other substituted monovalent hydrocarbon group in which at least part of hydrogen atoms bonded to carbon atoms has been substituted with a halogen atom, a cyano group or the like, such as chlorophenyl, fluorophenyl and cyanoethyl groups.

The a of the general formula (4) is an integer of 4 or more, preferably 10 to 540, b is an integer of 2 or more, preferably 5 to 270, and c is an integer of 0 or more, preferably 3 to 450.

The copolymer of the present invention has an average molecular weight of 800 to 200,000, preferably 2,000 to 100,000.

Specific examples of the copolymer of the present invention include, for example, those represented by the following formulas but are not particularly limited thereto.

wherein a and b are an integer satisfying $a \geq 4$, $b \geq 2$ and $6 \leq a+b \leq 2,300$.

wherein Bu stands for an butyl group, and a and b are an integer satisfying $a \geq 4$, $b \geq 2$ and $6 \leq a+b \leq 2,300$.

wherein Bu stands for an butyl group, Ph stands for a phenyl group, and a, b and c are an integer satisfying $a \geq 4$, $b \geq 2$, $0 \leq c \leq 1,000$ and $6 \leq a+b+c \leq 2,300$.

wherein Bu stands for an butyl group, and a, b and-c are an integer satisfying $a \geq 4$, $b \geq 2$, $0 \leq c \leq 1,000$ and $6 \leq a+b+c \leq 2,300$.

wherein Bu stands for an butyl group, and a, b and c are an integer satisfying $a \geq 4$, $b \geq 2$, $0 \leq c \leq 1,000$ and $6 \leq a+b+c > 2,300$.

Process for Producing Organosiloxane Copolymers

The production process of the present invention comprises subjecting the cyclotrisiloxane of said formula (5) and optionally together with the cyclotrisiloxane of said general formula (6) to ringopening polymerization in the presence of the lithium compound of said general formula (7), and then reacting the resulting reaction mixture with an acid or the organohalosilane of said general formula (8).

(i) Cyclotrisiloxane of the General Formula (6)

The cyclotrisiloxane of the general formula (6) is, if necessary, used for introducing a unit represented by the following general formula:

wherein $R^5$ and $R^6$ are as defined above into the copolymer of the present invention. $R^5$ and $R^6$ in the general formula (6) are the same as mentioned above.

Specific examples of the cyclotrisiloxane of the general formula (6) include, for example, hexamethylcyclotrisiloxane, hexaethylcyclotrisiloxane, hexaphenylcyclotrisiloxane, hexavinylcyclotrisiloxane, 1,3,5-trimethyl-1,3,5-triphenylcyclotrisiloxane, 1,3,5-trimethyl-1,3,5-trivinylcyclotrisiloxane, 1,3,5-trimethyl-1,3,5-tris(3,3,3-trifluoropropyl)cyclotrisiloxane and 1,3,5-trimethyl-1,3,5-tribenzylcyclotrisiloxane.

The amount of the cyclotrisiloxane of the general formula (6) used is 0 to 100 moles, preferably 0.1 to 50 moles, per mole of the cyclotrisiloxane of said formula (5).

(ii) Lithium Compound

The lithium compound used in the production process of the present invention is represented by the general formula (7) and acts as a catalyst for the ringopening polymerization reactions of both the cyclotrisiloxane having the general formula (5) and the cyclotrisiloxane having the general formula (6). $R^4$ in the general formula (7) is the same as in said $R^4$. The monovalent hydrocarbon group and the halogen-substituted alkyl group defined by $R^8$ and $R^9$ in the general formula (7) include the same as in said $R^5$ and $R^6$. The n in the general formula (7) is an integer of 0 or more, preferably 0 to 10.

Specific examples of the lithium compound include, for example, organolithium compounds, for example, alkyllithiums such as methyllithium, n-butyllithium, sec-butyllithium and tert-butyllithium; alkenyllithiums such as vinyllithium, allyllithium and hexenyllithium; aryllithiums such as phenyllithium and naphthyllithium; and aralkyllithiums such as benzyllithium and phenylethyllithium; lithium salts of organosilanes, such as lithium trimethylsilanolate, lithium dimethylvinylsilanolate and lithium diphenylmethylsilanolate; and lithium salts of organopolysiloxanes represented by the following general formula:

$$R^{10}\text{—}(Me_2SiO)_3\text{—}Li$$

wherein $R^{10}$ is a methyl group or a butyl group, and Me stands for a methyl group.

Among these lithium compounds, for example, the compound where in said general formula (7), n is 0 may be commercially available, while the compounds where in the same formula, n is 1 or more can be readily obtained by reacting an organosilane containing a silanol group, an organopolysiloxane containing a silanol group at one end of the molecular chain or an organocyclopolysiloxane with said lithium compound where n=0.

(iii) Acid or Organohalosilane

The production process of the present invention comprises subjecting said cyclotrisiloxane to ringopening polymerization, and stopping the polymerization reaction by adding an acid or the organohalosilane of the general formula (8) to the resulting reaction mixture. When said acid is used for stopping the polymerization reaction, a copolymer where in the general formula (4), A is a hydrogen atom can be obtained, while, when the organohalosilane is used, a copolymer where A is said organosilyl group can be obtained. Further, when the organohalo-silane is an organohydrogenhalosilane, A becomes a group containing a hydrogen atom bonded to a silicon atom. Accordingly, into the copolymer of the present invention having a group A containing a hydrogen atom bonded to a silicon atom, various functional groups can be introduced via the group A. Particularly, a copolymer where the thus introduced functional group is a reactive group is useful as a macromonomer.

The acids include, for example, organic acids such as formic acid, acetic acid, propionic acid, citric acid and benzoic acid; and inorganic acids such as carbonic acid, hydrochloric acid and sulfuric acid.

The organohalosilanes include, for example, trimethylchlorosilane, dimethylchlorosilane, vinyldimethylchlorosilane, (3-acryloyloxypropyl) dimethylchlorosilane, (3-methacryloyloxypropyl) dimethylchlorosilane, (4-styryl)dimethylchlorosilane, dimethylhydrogenchlorosilane, trimethylbromosilane, dimethylbromosilane, vinyldimethylbromosilane, (3-acryloyloxypropyl)dimethylbromosilane, (3-methacryloyloxypropyl)dimethylbromosilane, (4-styryl) dimethylbromosilane and dimethylhydrogenbromosilane.

The amount of said acid or organohalosilane used is generally 1 to 5 moles, preferably 1 to 2 moles, per mole of the lithium compound used.

In the production process of the present invention, although reactions such as said ringopening polymerization proceed even without using a reaction solvent, it is possible that the reactions proceed more favorably in an organic solvent to produce the copolymer of the present invention in high yield.

The organic solvents include, for example, ether reaction solvents such as diethyl ether, tetrahydrofuran, 1,4-dioxane and diethylene glycol dimethyl ether; non-proton solvents such as dimethyl sulfoxide and dimethylformamide; and organic solvents such as hexane, decane, benzene, toluene and xylene. They may be used singly or in a combination of two or more thereof. Particularly by combining a low-polar reaction solvent such as toluene with a high-polar reaction solvent such as tetrahydrofuran and dimethylformamide, it is possible that the reactions proceed more favorably. The amount of the reaction solvent used is preferably such an amount that the concentration of said cyclotrisiloxane is 5 to 90% by weight.

The temperature of the ringopening polymerization reaction may be about −20° to 50° C. By setting the temperature to such a range, the polymerization reaction proceeds more favorably. When the solvent is used, the temperature is preferably below the boiling point thereof. The reaction time may be about 10 minutes to 24 hours. Further, it is preferred that after adding the acid or the organohalosilane, the reaction mixture is stirred and aged for a predetermined period of time. The aging temperature may be about 0° to 50° C., and the aging time may be about 5 minutes to 5 hours.

The thus obtained copolymer of the present invention can be used as silicone fluids which are a known use and, in addition thereto, as a starting material for cosmetics and greases.

EXAMPLES

Example 1

Figure 1:
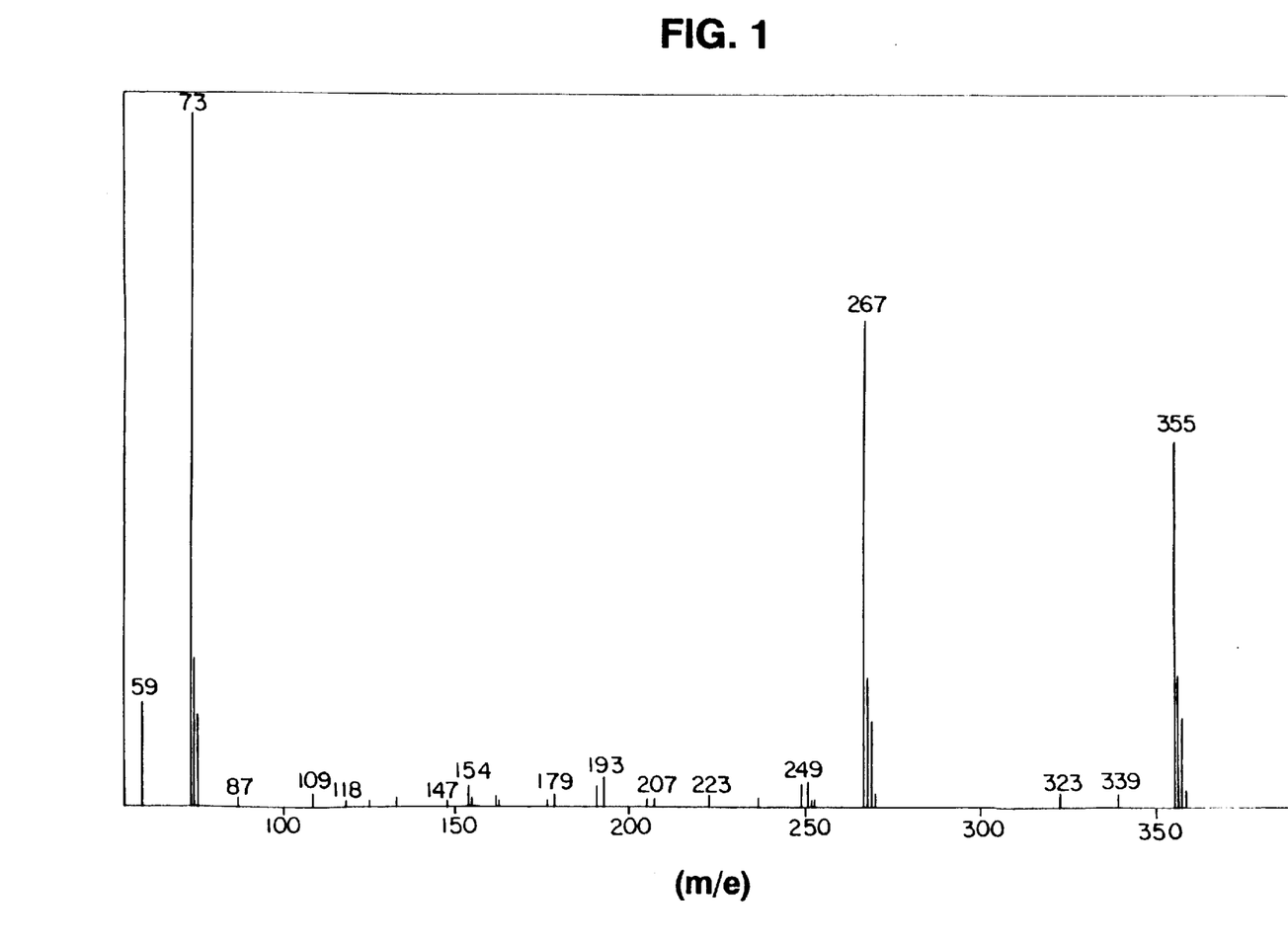
FIG. 1 is a GC-MS chart of the cyclotrisiloxane obtained in Example 1.

Into a four-necked flask, 160 g (1.58 moles) of triethylamine and 500 g of toluene were charged and then stirred until they were uniform. Then, while maintaining the temperature of the content in the flask at 0° to 10° C., a solution of 250 g (0.79 mole) of a silanol group-containing organosiloxane represented by said formula (2) dissolved in 200 g of methyl ethyl ketone and a solution of 102 g (0.79 mole) of dimethyldichlorosilane dissolved in 350 g of toluene were simultaneously added dropwise into the flask over 2 hours. After the completion of the addition, the content of the flask was stirred for 1 hour, and the resulting reaction mixture was washed with water and was vacuum distilled at 64° C. (boiling point) under 2.5 Torr to produce 167 g (yield: 55%) of a colorless transparent liquid reaction product. The reaction product was confirmed to be 1,3-bis(trimethylsiloxy)-1,3,5,5-tetramethylcyclotrisiloxane from the results of gas chromatography and mass spectrometric analysis (hereinafter, referred to as GC-MS analysis) and of measurements for $^1$H-NMR and IR absorption. Incidentally, the results of GC-MS analysis and of measurements for IR absorption and $^1$H-NMR are given below; and the GC-MS chart is shown in FIG. 1, the IR chart in FIG. 2, and the $^1$H-NMR chart in FIG. 3.

(GC-MS analysis)

Figure 2:
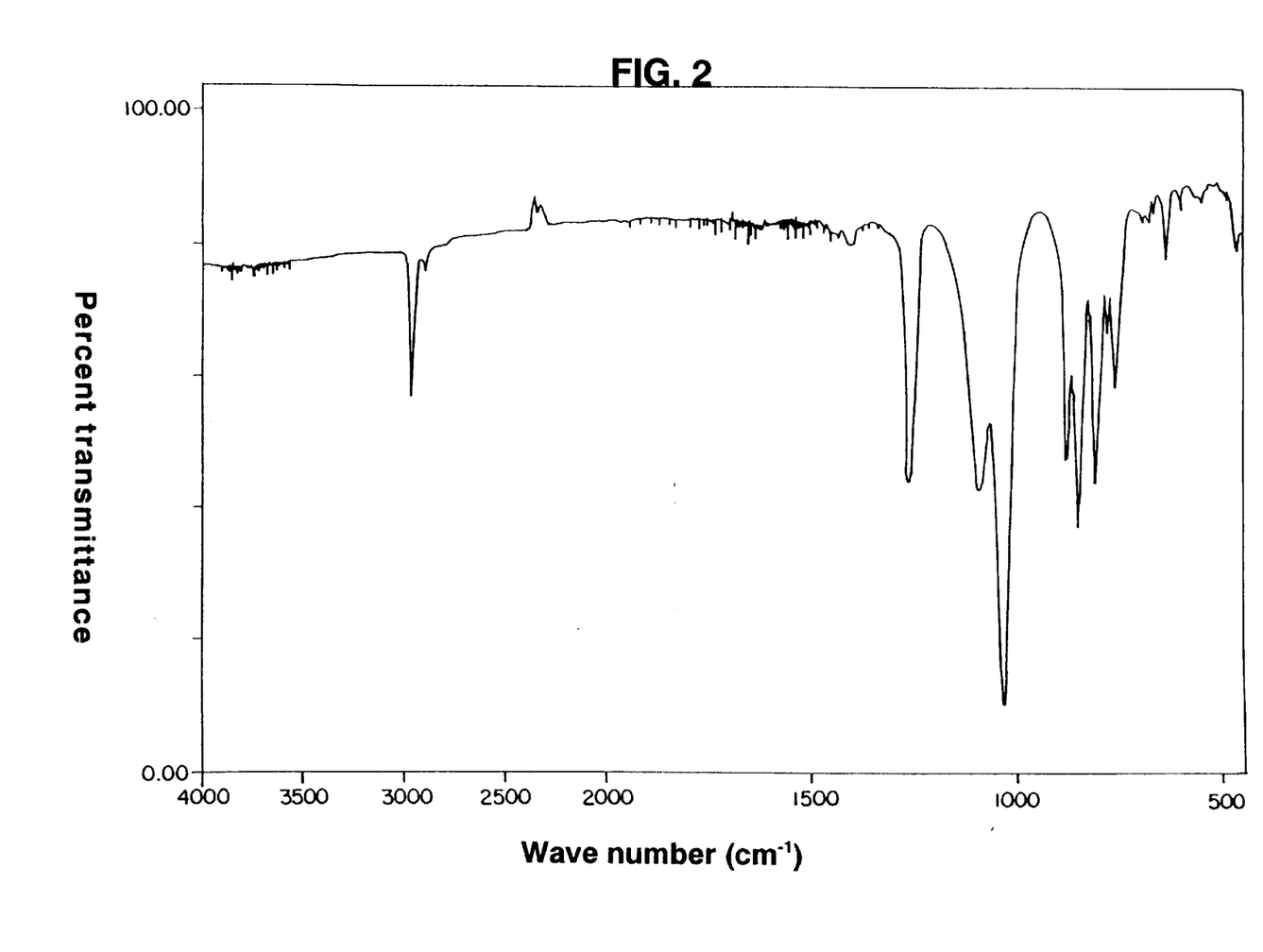
FIG. 2 is an IR chart of the cyclotrisiloxane obtained in Example 1.
Figure 3:
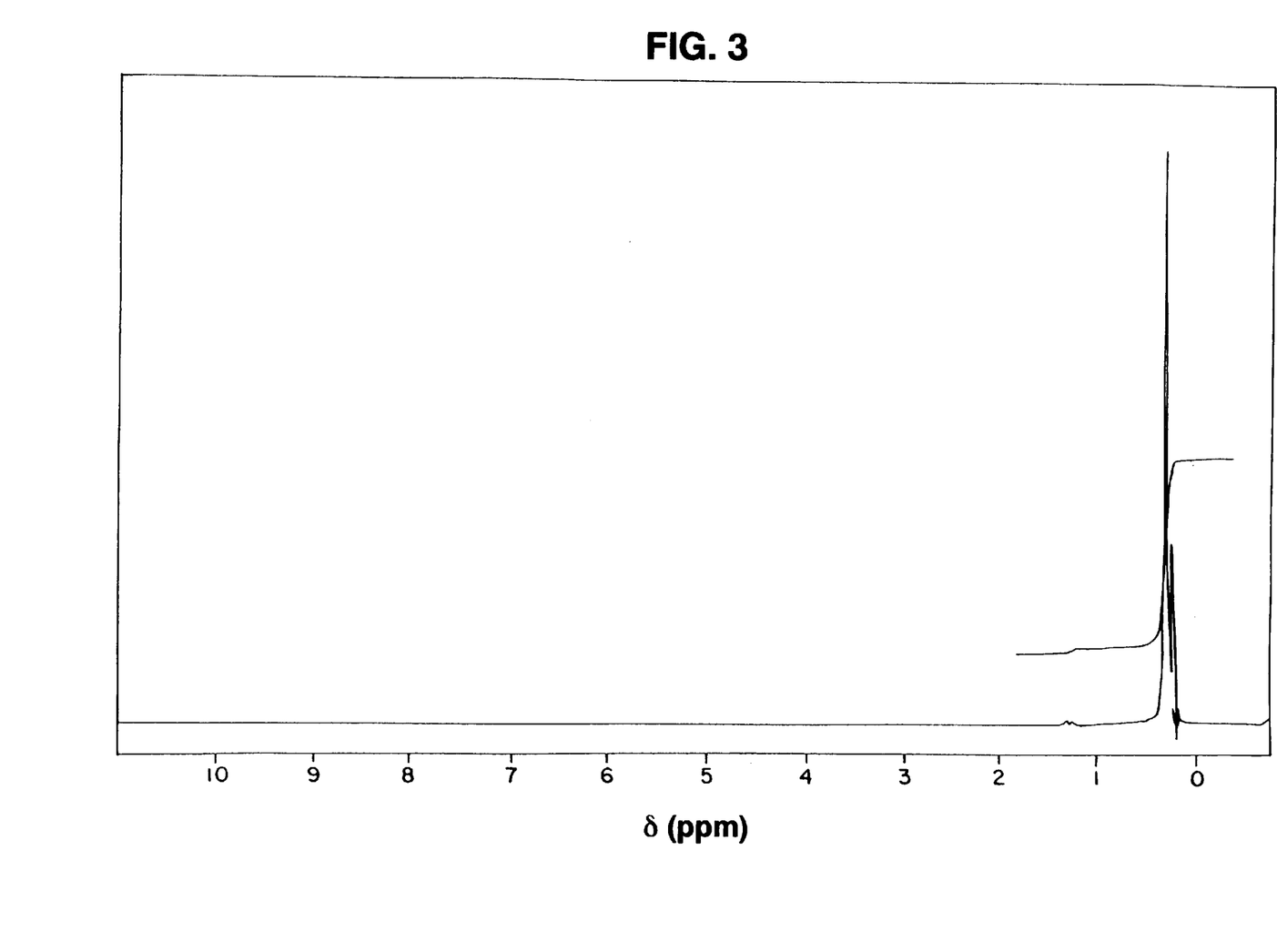
FIG. 3 is a $^1$H-NMR chart of the cyclotrisiloxane obtained in Example 1.

$[M\text{—}CH_3]^+ = 355$ (IR absorption analysis)
    1,020 cm$^{-1}$: Si—O
    1,085 cm$^{-1}$: O—SiCH$_3$
($^1$H-NMR measurement)
    δ0.15–0.5 ppm (Si—CH$_3$ 30H)

Example 2

Figure 4:
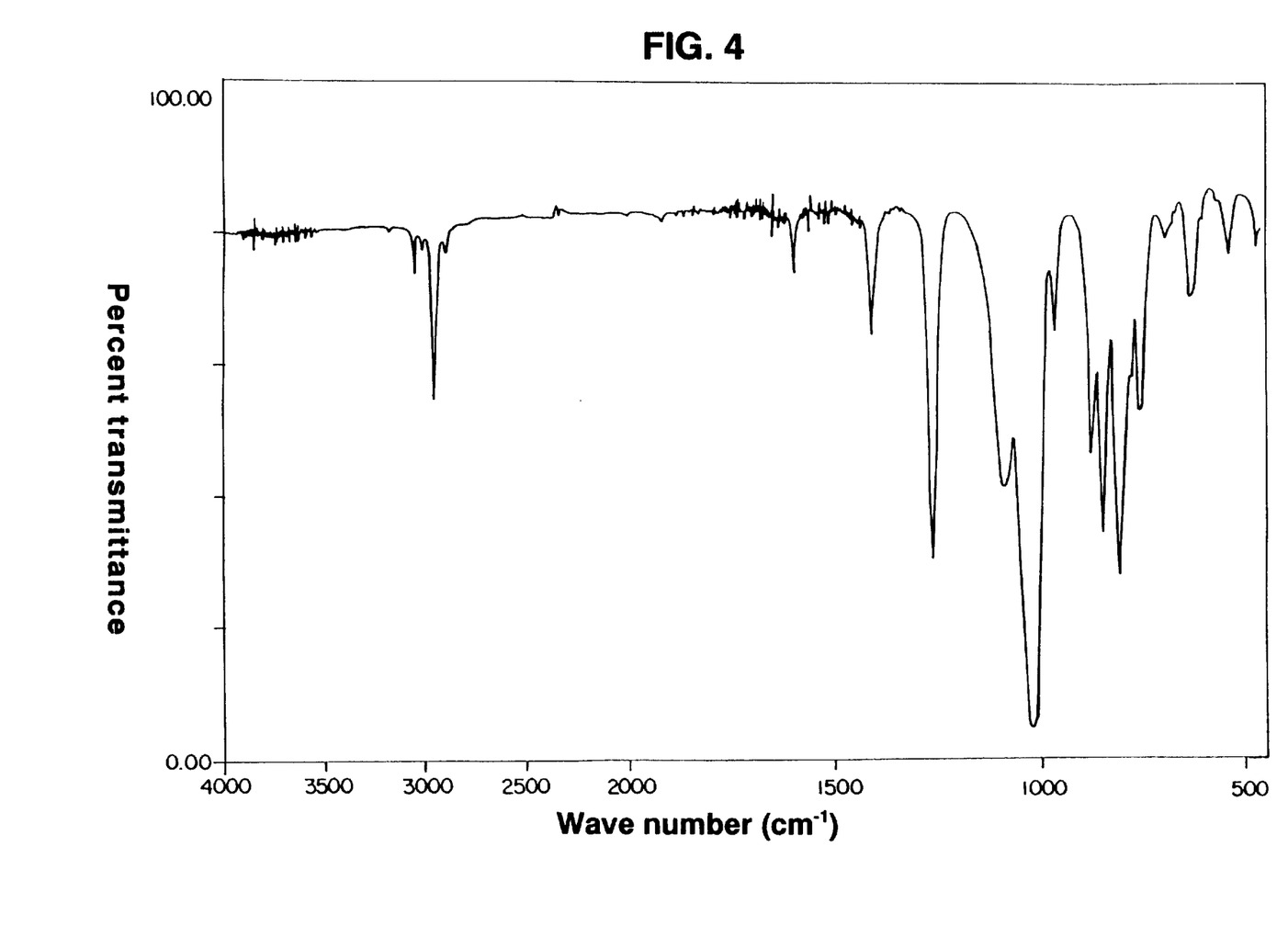
FIG. 4 is an IR chart of the cyclotrisiloxane obtained in Example 2.

Into a four-necked flask, 202 g (2.0 moles) of triethylamine and 500 g of toluene were charged and then stirred until they were uniform. Then, while maintaining the temperature of the content in the flask at 0° to 10° C., a solution of 314 g (1.0 mole) of a silanol group-containing organosiloxane represented by said formula (2) dissolved in 100 g of toluene and a solution of 141 g (1.0 mole) of vinylmethyldichlorosilane dissolved in 250 g of toluene were simultaneously added dropwise into the flask over 2 hours. After the completion of the addition, the content of the flask was stirred for 30 minutes, and the resulting reaction mixture was washed with water and was vacuum distilled at 74° C. (boiling point) under 3 Torr to produce 156 g (yield: 41%) of a colorless transparent liquid reaction product. The reaction product was confirmed to be 1,3-bis(trimethylsiloxy)-1,3,5-trimethyl-5-vinylcyclotrisiloxane from the results of GC-MS analysis and of measurements for $^1$H-NMR and IR absorption. Incidentally, the results of GC-MS analysis and of measurements for IR absorption and $^1$H-NMR are given below, and the IR chart is shown in FIG. 4.

(GC-MS analysis) [M—CH$_3$]$^+$=367
(IR absorption analysis)
    1,020 cm$^{-1}$: Si—O
    1,085 cm$^{-1}$: O—SiCH$_3$
    1,595 cm$^{-1}$: Si—CH=CH$_2$
($^1$H-NMR measurement)
    δ0.15–0.5 ppm (Si—CH$_3$ 27H)
    δ5.5–5.8 ppm (Si—CH=CH$_2$ 3H)

Example 3

Figure 5:
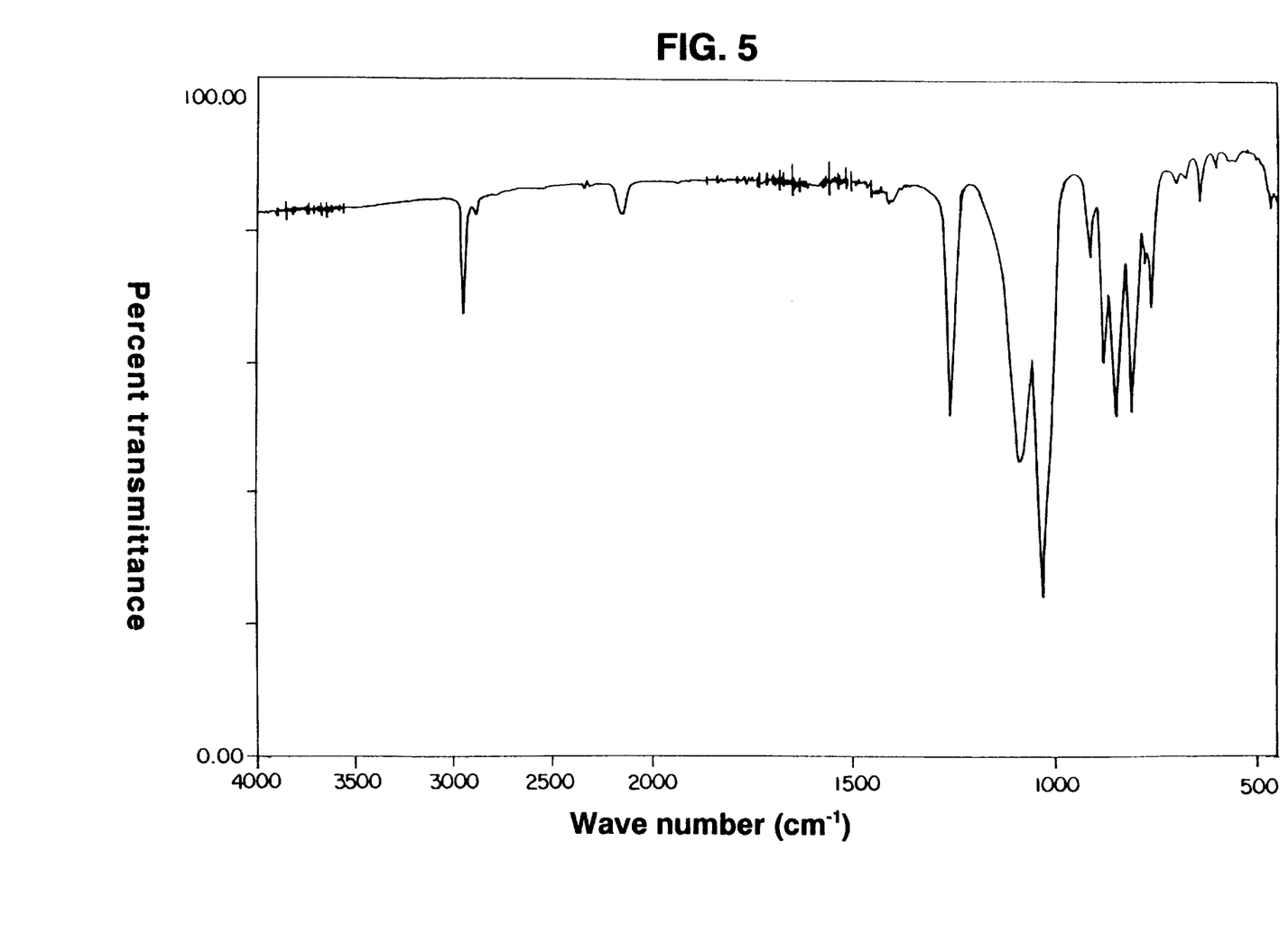
FIG. 5 is an IR chart of the cyclotrisiloxane obtained in Example 3.

Into a four-necked flask, 30.3 g (0.3 mole) of triethylamine and 100 g of toluene were charged and then stirred until they were uniform. Then, while maintaining the temperature of the content in the flask at 0° to 5° C., a solution of 47.1 g (0.15 mole) of a silanol group-containing organosiloxane represented by said formula (2) dissolved in 60 g of 1,4-dioxane and a solution of 17.3 g (0.15 mole) of methyldichlorosilane dissolved in 100 g of toluene were simultaneously added dropwise into the flask over 1 hours. After the completion of the addition, the content of the flask was stirred for 1 hour, and the resulting reaction mixture was washed with water and was vacuum distilled at 60° C. (boiling point) under 3 Torr to produce 21 g (yield: 40%) of a colorless transparent liquid reaction product. The reaction product was confirmed to be 1,3-bis(trimethylsiloxy)-1,3,5-trimethylcyclotrisiloxane from the results of GC-MS analysis and of measurements for $^1$H-NMR and IR absorption. Incidentally, the results of GC-MS analysis and of measurements for IR absorption and $^1$H-NMR are given below, and the IR chart is shown in FIG. 5.
(GC-MS analysis)
    [M—H]$^+$=355
(IR absorption analysis)
    1,020 cm$^{-1}$: Si—O
    1,085 cm$^{-1}$: O—SiCH$_3$
    2,158 cm$^{-1}$: Si—H ($^1$H-NMR measurement)
    δ0.15–0.5 ppm (Si—CH$_3$ 27H)
    δ4.3–4.6 ppm (Si—H 1H)

Example 4

Into a four-necked flask, 10 g (128 m mole) of pyridine and 50 g of toluene were charged and then stirred until they were uniform. Then, while maintaining the temperature of the content in the flask at 0° to 10° C., a solution of 20 g (64 m mole) of a silanol group-containing organosiloxane represented by said formula (2) dissolved in 50 g of toluene and a solution of 16.1 g (64 m mole) of diphenyldichlorosilane dissolved in 50 g of toluene were simultaneously added dropwise into the flask over 30 minutes. After the completion of the addition, the content of the flask was stirred for 15 minutes, and the resulting reaction mixture was washed with water and was vacuum distilled at 150° C. (boiling point) under 1 Torr to produce 20 g (yield: 65%) of a colorless transparent liquid reaction product. The reaction product was confirmed to be 1,3-bis(trimethylsiloxy)-5,5-diphenyl-1,3-dimethylcyclotrisiloxane from the results of GC-MS analysis and of measurements for $^1$H-NMR and IR absorption. Incidentally, the results of GC-MS analysis and of measurements for IR absorption and $^1$H-NMR are given below.

(GC-MS analysis)
    [M]$^+$=494
(IR absorption analysis)
    1,020 cm$^{-1}$: Si—O
    1,085 cm$^{-1}$: O—SiCH$_3$
($^1$H-NMR measurement)
    δ0.2–0.8 ppm (Si—CH$_3$ 24H)
    δ7.3–7.8 ppm (Si—C$_6$H$_5$ 10H)

Example 5

Into a four-necked flask which was inside replaced with a dry nitrogen gas, 30 g (80 m mole) of 1,3-bis(trimethylsiloxy)-1,3,5,5-tetramethylcyclotrisiloxane obtained in Example 1 and 100 g of tetrahydrofuran were charged. Then, the content of the flask was kept at 0° to 10° C., and 0.96 g (10 m mole) of lithium trimethylsilanolate was charged therein while stirring the content of the flask, followed by aging for 10 minutes. Thereafter, 1.3 g of trimethylchlorosilane was added into the flask, the content of the flask was stirred for 30 minutes, and the reaction was stopped. After the resulting reaction product was washed with water, the solvent was evaporated off to produce a colorless transparent liquid silicone fluid (yield: 80%). The obtained silicone fluid was subjected to differential thermal analysis (DSC) to evaluate the low-temperature characteristics thereof. The result is shown in Table 1. Incidentally, the low-temperature characteristics of a dimethylpolysiloxane represented by the following formula:

as a control, was evaluated by differential thermal analysis. The result is also shown in Table 1.

TABLE 1

| | Peaks of melting point |
|---|---|
| Silicone fluid of Example 5 | Not detected. |
| Dimethylpolysiloxane (control) | −39° C. and −51° C. |

(Evaluation)

In the control dimethylpolysiloxane, peaks of melting point by differential thermal analysis were observed at −39° C. and −51° C. On the contrary, in the silicone fluid produced from the cyclotrisiloxane of the present invention, any peaks of melting point were not observed, and the silicone fluid exhibited flowability free of solidification in the range of from room temperature to low temperatures and was very excellent in low-temperature characteristics.

Example 6

Figure 6:
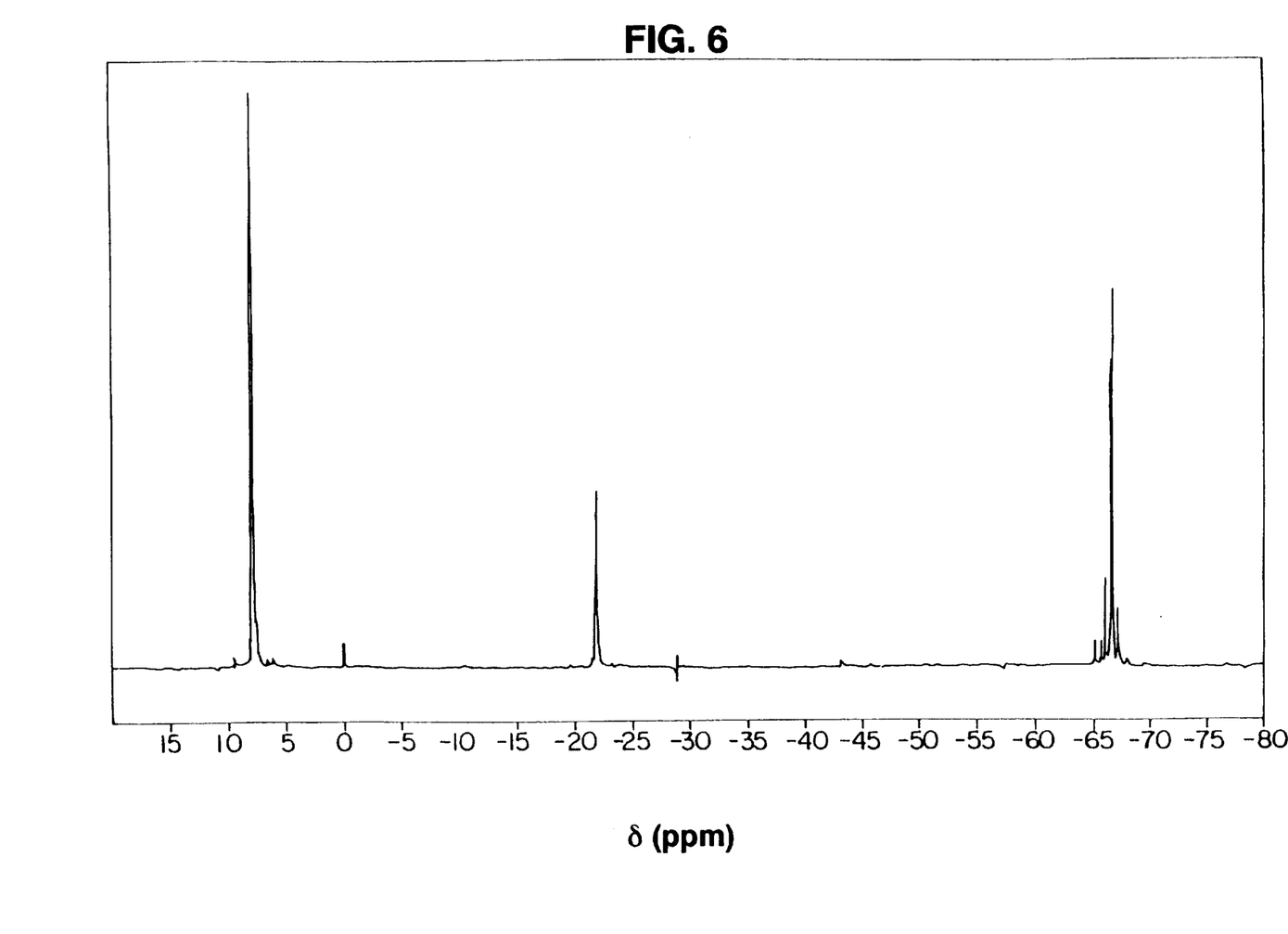
FIG. 6 is a $^{29}$Si-NMR chart of the copolymer obtained in Example 6.
Figure 7:
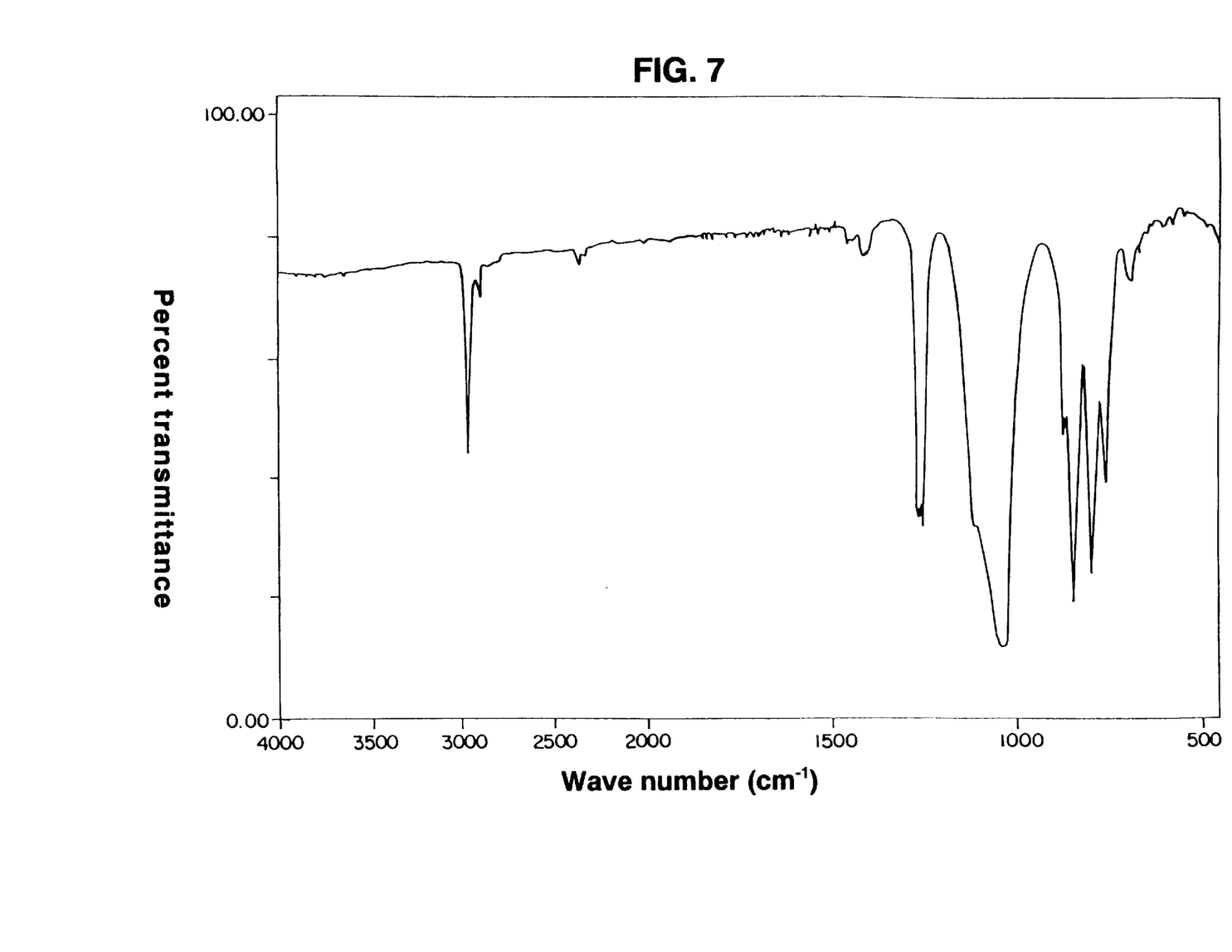
FIG. 7 is an IR chart of the copolymer obtained in Example 6.

The inside of a four-necked flask was replaced with a dry nitrogen gas, and into the flask, 30 g (80 m mole) of the cyclotrisiloxane of said formula (5) and 100 g of tetrahydrofuran were charged. Then, the content of the flask was maintained at 0° to 5° C., and 0.77 g (8.0 m mole) of lithium trimethylsilanolate was charged therein with stirring to effect polymerization reaction. The content of the flask was stirred for 20 minutes for aging. Then, 1.0 g of trimethylchlorosilane was charged in the content of the flask and stirred for 30 minutes to stop the polymerization reaction. After the resulting reaction mixture was washed with water, the tetrahydrofuran was evaporated off by vacuum distillation to produce a colorless transparent liquid reaction product (yield: 80%). The reaction product was confirmed, from the results of gel permeation chromatography (hereinafter, referred to as GPC) analysis, to be a polymer having a number-average molecular weight (hereinafter, referred to as Mn) of 3,600 and a molecular weight distribution (Mn/Mw wherein Mw stands for a weight-average molecular weight, the same being applied hereinafter) of 1.33. Also, from the results of $^{29}$Si-NMR analysis of the reaction product, it was observed that the absorption peak of a trimethylsiloxy group was at a position of 7.8 ppm. Simultaneously, IR absorption measurement of the reaction product was conducted. The $^{29}$Si-NMR chart is shown in FIG. 6, the IR chart in FIG. 7. From the results of said GPC analysis, $^{29}$Si-NMR analysis and IR absorption measurement, the obtained reaction product was confirmed to be an organosiloxane copolymer represented by the following compositional formula:

wherein Me stands for a methyl group.

Example 7

Figure 8:
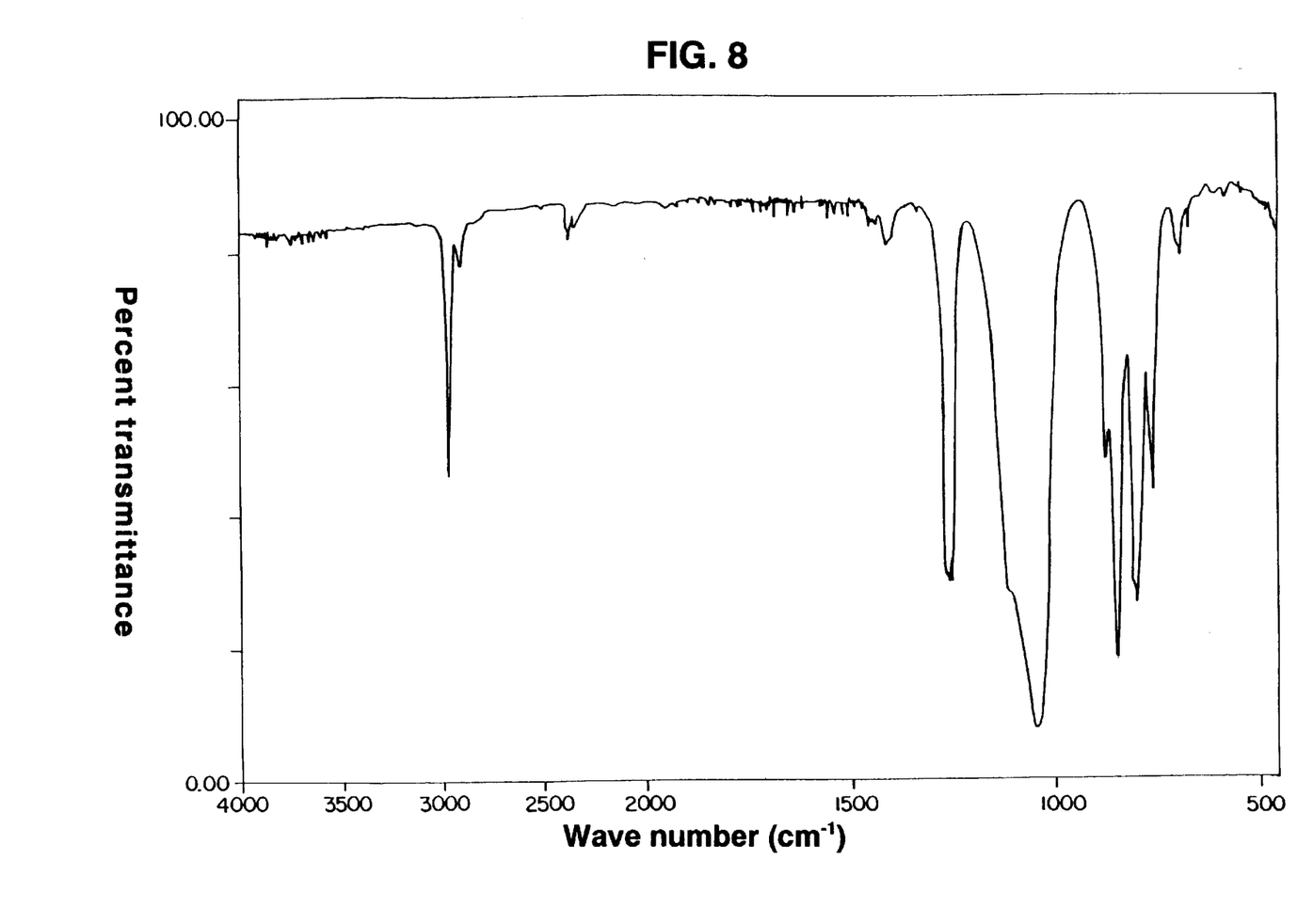
FIG. 8 is an IR chart of the copolymer obtained in Example 7.

The inside of a four-necked flask was replaced with a dry nitrogen gas, and into the flask, 30 g (80 m mole) of the cyclotrisiloxane of said formula (5) and 100 g of tetrahydrofuran were charged. Then, the content of the flask was maintained at 0° to 5° C., and 0.34 ml (0.54 m mole as n-butyllithium) of a hexane solution (content of n-butyllithium: 1.6 mole/liter) of n-butyllithium was charged therein with stirring to effect polymerization reaction. The content of the flask was stirred for 20 minutes for aging. Then, 0.1 g of trimethylchlorosilane was charged in the content of the flask and stirred for 50 minutes to stop the polymerization reaction. After n-hexane was added to the resulting reaction mixture and washed with water, the tetrahydrofuran and hexane were evaporated off by vacuum distillation to produce a colorless transparent liquid reaction product (yield: 65%). The reaction product was confirmed, from the results of GPC analysis, to be a polymer having a Mn of 54,000 and a molecular weight distribution (Mn/Mw) of 1.38. Also, from the results of $^{29}$Si-NMR analysis of the reaction product, it was observed that the absorption peak of a trimethylsiloxy group was at a position of 7.8 ppm. Simultaneously, IR absorption measurement of the reaction product was conducted. The IR chart is shown in FIG. 8. From the results of said GPC analysis, $^{29}$Si-NMR analysis and IR absorption measurement, the obtained reaction product was confirmed to be an organosiloxane copolymer represented by the following compositional formula:

wherein Me stands for a methyl group, and Bu stands for a butyl group.

Example 8

Figure 9:
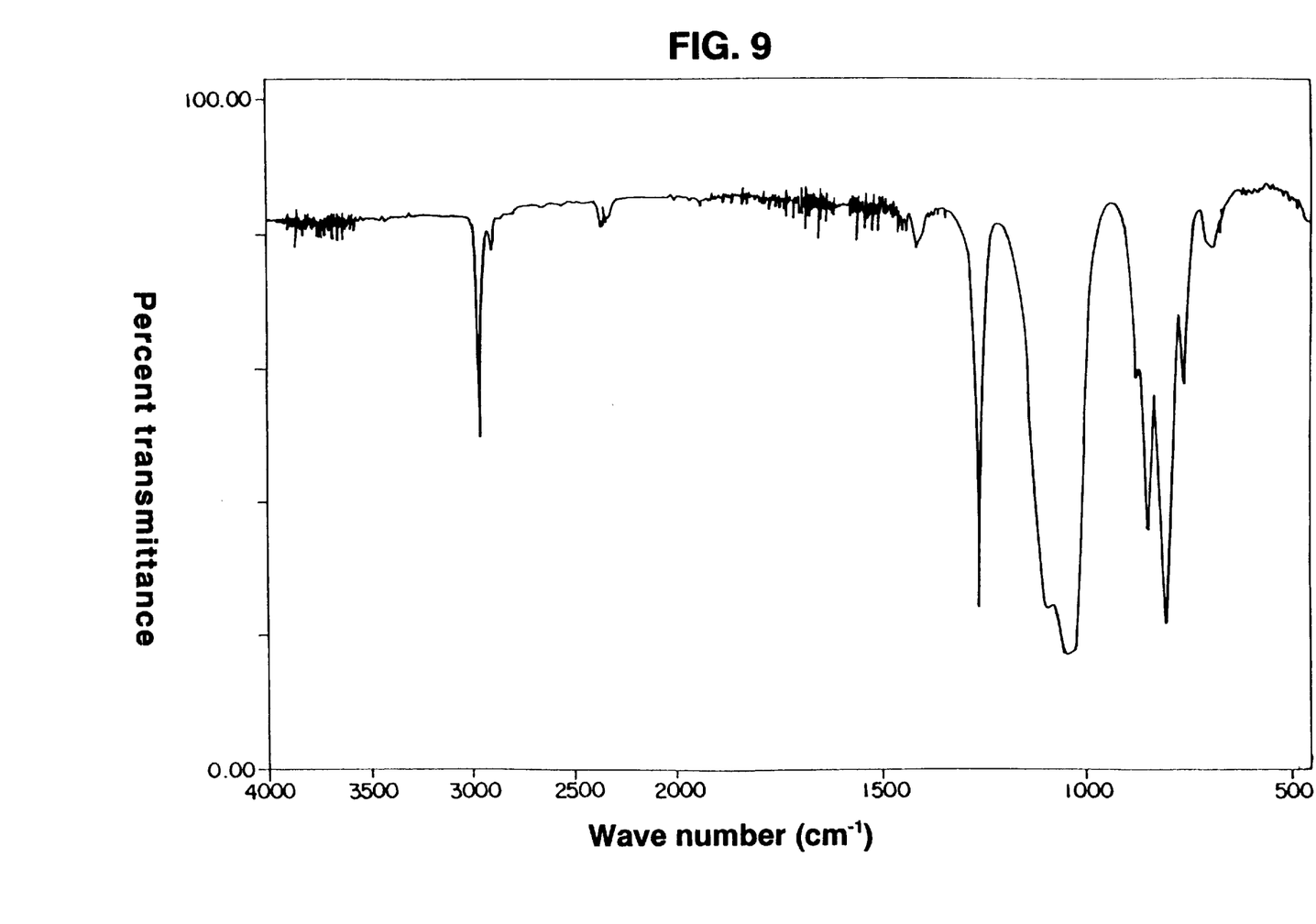
FIG. 9 is an IR chart of the copolymer obtained in Example 8.

The inside of a four-necked flask was replaced with a dry nitrogen gas, and into the flask, 0.48 g (5.0 m mole) of lithium trimethylsilanolate and 50 g of tetrahydrofuran were charged. Then, the content of the flask was maintained at 0° to 5° C., and a solution of both 22.2 g (60 m mole) of the cyclotrisiloxane of said formula (5) and 13.3 g (60 m mole) of hexamethylcyclotrisiloxane dissolved in 100 g of tetrahydrofuran were added dropwise to the content over 3 hours with stirring to effect polymerization reaction. The content of the flask was stirred for 15 minutes for aging. Then, 1.0 g of trimethylchlorosilane was charged in the content of the flask and stirred for 30 minutes to stop the polymerization reaction. After the resulting reaction mixture was washed with water, the tetrahydrofuran was evaporated off by vacuum distillation to produce a colorless transparent liquid reaction product (yield: 85%). The reaction product was confirmed, from the results of GPC analysis, to be a polymer having a Mn of 7,000 and a molecular weight distribution (Mn/Mw) of 1.31. Also, from the results of $^{29}$Si-NMR analysis of the reaction product, it was observed that the absorption peak of a trimethylsiloxy group was at a position of 7.8 ppm. Simultaneously, IR absorption measurement of the reaction product was conducted. The IR chart is shown in FIG. 9. From the results of said GPC analysis, $^{29}$Si-NMR analysis and IR absorption measurement, the obtained reaction product was confirmed to be an organosiloxane copolymer represented by the following compositional formula:

wherein Me stands for a methyl group.

Example 9

The inside of a four-necked flask was replaced with a dry nitrogen gas, and into the flask, 30 g (80 m mole) of the cyclotrisiloxane of said formula (5), 80 g of toluene and 5 g of dimethyl sulfoxide were charged. Then, the content of the flask was maintained at 0° to 10° C., and 0.38 g (4.0 m mole) of lithium trimethylsilanolate was charged therein with stirring. Aging was conducted for 30 minutes while stirring the content of the flask. To the content of the flask, 40 ml of 0.1 N—HCl was then added and stirred for 10 minutes to stop the reaction. After the resulting reaction mixture was washed with water, the solvent was evaporated off by vacuum distillation to produce a colorless transparent liquid reaction product (yield: 80%). The reaction product was confirmed, from the results of GPC analysis, to be a polymer having a Mn of 3,600 and a molecular weight distribution (Mn/Mw) of 1.32. Also, from the results of $^{29}$Si-NMR analysis of the reaction product, it was observed that the absorption peak of a trimethylsiloxy group was at a position of 7.8 ppm. Simultaneously, IR absorption measurement of the reaction product was conducted. From the results of said GPC analysis, $^{29}$Si-NMR analysis and IR absorption measurement, the obtained reaction product was confirmed to be an organosiloxane copolymer represented by the following compositional formula:

Me[Me$_3$SiO(Me)SiO]$_{36}$(Me$_2$SiO)$_{18}$H wherein Me stands for a methyl group.

Example 10

The same manner as in Example 8 was repeated except that the amount of lithium trimethylsilanolate used was changed to 1.92 g (20 m mole) from 0.48 g and the amount of hexamethylcyclotrisiloxane used was changed to 66.6 g (0.3 mole) from 13.3 g, to produce a copolymer represented by the following compositional formula:

Me[Me$_3$SiO(Me)SiO]$_5$(Me$_2$SiO)$_{90}$SiMe$_3$ wherein Me stands for a methyl group.

Example 11

The copolymers obtained in Examples 6, 8 and 10 and an organopolysiloxane for comparison represented by the following compositional formula:

Me(Me$_2$SiO)$_{85}$SiMe$_3$ wherein Me stands for a methyl group were subjected to measurement by differential thermal analysis (DSC). The results are shown in Table 2, and the DSC chart is shown in FIG. 10.

Figure 10:
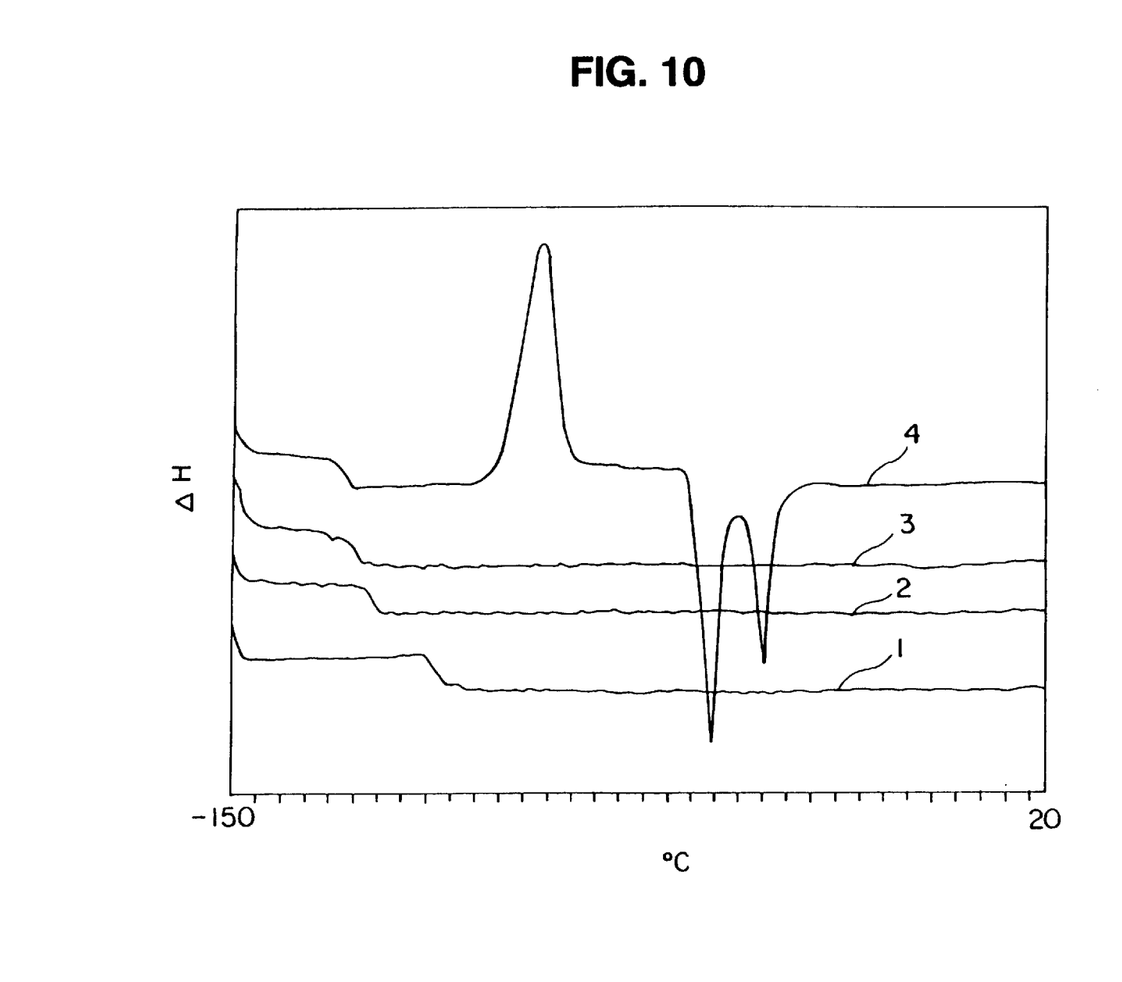

In FIG. 10, reference numeral 1 represents a DSC graph of the copolymer obtained in Example 6, reference numeral 2 a DSC graph of the copolymer obtained in Example 8, reference numeral 3 a DSC graph of the copolymer obtained in Example 10, and reference numeral 4 a DSC graph of the organopolysiloxane for comparison.

TABLE 2

|  | Measurement of melting point by DSC |
| --- | --- |
| Copolymer of Example 6 | NO peaks of melting point were detected. |
| Copolymer of Example 8 | No peaks of melting point were detected. |
| Copolymer of Example 10 | NO peaks of melting point were detected. |
| Polymer for comparison | −39° C. and −51° C. |

As is apparent from the results of Table 2, the copolymers of the present invention each exhibit flowability free of solidification in the range of from room temperature to low temperatures and are excellent in low-temperature characteristics.

What is claimed is:

1. An organosiloxane copolymer represented by the following general formula (4):

wherein $R^4$ is a monovalent hydrocarbon group; $R^5$ and $R^6$ are independently a monovalent hydrocarbon group or a halogenated alkyl group; A is a hydrogen atom or an organosilyl group represented by the following general formula:

—Si(R$^7$)$_3$ wherein plural $R^7$ are independently a hydrogen atom or a monovalent organic group, provided that at least one of plural $R^7$ is a monovalent organic group; a is an integer of 4 or more; b is an integer of 2 or more; and c is an integer of 0 or more.

2. A process for producing the organosiloxane copolymer of claim 1, which comprises the steps of subjecting a cyclotrisiloxane represented by the following formula (5):

to ringopening polymerization in the presence of a lithium compound represented by the following general formula (7):

R$^4$(R$^8$R$^9$SiO)$_n$Li          (7)

wherein $R^4$ is a monovalent hydrocarbon group, $R^8$ and $R^9$ are independently a monovalent hydrocarbon group or a halogenated alkyl group, and n is an integer of 0 or more, and adding to the resulting reaction mixture an acid or an organohalosilane represented by the following general formula (8):

XSi(R$^7$)$_3$          (8)

wherein X is a halogen atom, and plural $R^7$ are independently a hydrogen atom or a monovalent organic group, provided that at least one of plural $R^7$ is a monovalent organic group, to stop the ringopening polymerization.

3. The process according to claim 2, wherein the cyclo trisiloxane of the formula (5) is subjected to the ringopening polymerization together with a cyclotrisiloxane represented by the following general formula (6)

wherein $R^5$ and $R^6$ are independently a monovalent hydrocarbon group or a halogenated alkyl group.

* * * * *